United States Patent [19]

Buckwalter et al.

[11] 4,443,473
[45] Apr. 17, 1984

[54] CARBAMATE DERIVATIVES

[75] Inventors: Brian L. Buckwalter, Yardley, Pa.; Thomas R. LaHann, Cleves, Ohio

[73] Assignee: The Procter & Gamble Company, Cincinnati, Ohio

[21] Appl. No.: 384,685

[22] Filed: Jun. 3, 1982

Related U.S. Application Data

[63] Continuation-in-part of Ser. No. 279,091, Jun. 30, 1981, abandoned.

[51] Int. Cl.³ .................... C07C 125/06; A61K 31/27
[52] U.S. Cl. ..................................... 424/300; 560/29; 260/455 A
[58] Field of Search ......................... 424/300; 560/29; 260/455 A

[56] References Cited

U.S. PATENT DOCUMENTS

| | | |
|---|---|---|
| 3,268,582 | 8/1966 | Zeile et al. |
| 3,452,084 | 6/1969 | Shavel et al. .................... 424/300 |
| 3,801,624 | 4/1974 | Biel et al. ....................... 424/300 |
| 3,832,365 | 8/1974 | Wehrli et al. |
| 3,983,164 | 9/1976 | Thorne et al. |
| 4,238,508 | 12/1980 | Nelson |
| 4,276,229 | 6/1981 | Lee |
| 4,313,958 | 2/1982 | LaHann ........................... 424/324 |

FOREIGN PATENT DOCUMENTS

| | | |
|---|---|---|
| 626897 | 5/1963 | Belgium |
| 2153801 | 5/1972 | Fed. Rep. of Germany ........ 560/29 |
| 2153825 | 5/1972 | Fed. Rep. of Germany ........ 560/29 |
| 1336388 | 8/1963 | France |
| 6139413 | 10/1981 | Japan |
| 6147752 | 11/1981 | Japan |

OTHER PUBLICATIONS

Brunner et al., "About P-methoxy—and 3,4-dimethoxyphenylurethanes," *Monatshefte fur chemie*, vol. 63, (1933), pp. 374–384.

Shaw, "The Relation of Structure Configuration to the Herbicidal Properties and Phytotoxicity of Several Carbamates and Other Chemicals," *Weeds*, vol. 2, (1953), pp. 43–65 (Chem. Abs. 47:11638b).

Templeman et al., "Differential Effect of Synthetic Growth Substances and Other Compounds on Plant Species: Seed Germination and Early Growth Responses to Some Arylcarbamic Esters and Related Compounds," *Proc. Roy Soc.* B133, (1946), pp. 480–485 (Chem. Abs. 41:7039h).

Verdino et al., "Condensation of Aromatic Amines with Cholesteryl Chloroformate," *Monatshefte fur Chemie*, vol. 65, (1934), pp. 141–152 (Chem. Abs. 29:1830).

Kiernan, "A Study of Chemically Induced Acute Inflammation in the Skin of the Rat", *Quart. J. Exp. Physiol.*, vol. 62, (1977), pp. 151–161.

Jansco et al., "Direct Evidence for Neurogenic Inflammation and its Prevention by Denervation and by Pretreatment with Capsaicin," *Br. J. Pharm. Chemother.*, vol. 31, (1967), pp. 138–151.

Arvier et al., "Modification by Capsaicin and Compound 40/80 of Dye Leakage Induced by Irritants in the Rat," *Br. J. Pharm.*, vol. 59, (1977), pp. 61–68.

Yaksh et al., "Intrathecal Capsaicin Depletes Substance P in the Rat Spinal Cord and Produces Prolonged Thermal Analgesia," *Science*, vol. 260, (1979), pp. 481–483.

Virus et al., "Pharmacologic Actions of Capsaicin: Apparent Involvement of Substance P and Serotonin," *Life Sciences*, vol. 24, (1979), pp. 1273–1281.

Jones et al., "The Relation Between Chemical Constitution and Pungency in Acid Amides," *J. Chem. Soc.*, vol. 27, (1925), pp. 2588–2598.

Newman, "Natural and Synthetic Pepper-Flavored Substances," *Chem. Prod.*, (Mar., 1954), pp. 102–106.

Szolesanyi et al., "Sensory Effects of Capsaicin Congeners," *Arzneim.-Forsch.*, vol. 25, (1975), pp. 1871–1881.

Szolesanyi et al., "Sensory Effects of Capsaicin Congeners," *Arzneim.-Forsch.*, vol. 26, (1976), pp. 33–37.

Hegyes et al., "Synthesis of Homovanillic Acid Derivatives of Capsaicin-Like Effect," *Acta. Phys. Chem.*, vol. 20, (1974), pp. 115–120.

Michalska et al., "Synthesis and Local Anesthetic Properties of N-substituted 3,4-Dimethoxyphenethylamine Derivatives," *Diss. Pharm. Pharmacol.*, vol. 24, (1972), pp. 17–25 (Chem. Abs. 77:19271a).

T. Szeki, "Contributions Towards Understanding the Relation Between the Chemical Constitution and the Sharp Taste of Acylamines," *Arch. Pharm.*, vol. 268, (1930), pp. 151–157.

*Primary Examiner*—James H. Reamer
*Attorney, Agent, or Firm*—Eric W. Guttag; Michael J. Roth; Steven J. Goldstein

[57] ABSTRACT

A compound, or pharmaceutically acceptable salt thereof, having the formula:

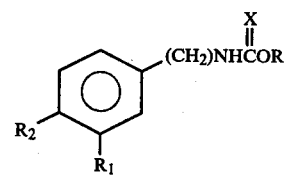

wherein X is O or S; wherein R is $C_3$–$C_{12}$ alkyl or aralkyl, branched or unbranched, aryl or haloaryl, $C_3$–$C_{22}$ alkenyl, branched or unbranched, or benzyl; wherein $R_1$ is H, OH or $OCH_3$, and $R_2$ is H or OH, at least one of $R_1$ and $R_2$ being OH or $OCH_3$. These carbamates have analgesic and anti-irritant activity when administered to humans and lower animals.

25 Claims, No Drawings

CARBAMATE DERIVATIVES

CROSS REFERENCE TO RELATED APPLICATIONS

The present application is a continuation-in-part of U.S. application, Ser. No. 279,091, filed June 30, 1981, now abandoned.

TECHNICAL FIELD

This invention provides certain novel carbamate derivatives having analgesic and anti-irritant activity.

In general, analgesics fall into two broad categories. The simple analgesics, such as aspirin, are most effective against pain of integumental origin, headache, and muscle aches; the narcotics are more useful for deep or visceral pain. Narcotic analgesics such as morphine also produce more profound effects than simple analgesics, and are potentially addicting, with the development of tolerance and physical dependence. The narcotic analgesics appear to work through interaction with the endorphin/enkephalin system of the CNS; many of the simple, non-narcotic analgesics appear to work by inhibition of prostaglandin synthetase. The effect of narcotics is to elevate the pain threshold above the normal level; the non-narcotic analgesics act to raise an abnormally low pain threshold to the normal level. The narcotic analgesics are antagonized by N-allyl compounds such as naloxone; the non-narcotic analgesics are not.

In the field of anti-irritancy, dermal and tissue irritation can be caused by common irritants such as acids and alkalis, keratolytics and proteolytics, depilatories, plant oils, and the like. In many instances, it is observed that compounds which effectively block the action of one class of irritants are totally or substantially ineffective with other classes of irritants. The problem in the art has been compounded by the inadequacy, or unavailability in some cases, of appropriate animal models of dermal irritation. For example, most laboratory animals are insensitive to poison ivy. As a consequence, the search has long continued, in a purely empirical way, for anti-irritant compositions—not always successfully.

The present invention relates to the discovery that certain novel carbamate derivatives are analgesics and anti-irritants. In their analgesic action, these compounds appear to be largely unrelated to the two known classes of analgesics. In certain tests, these compounds produce a level of analgesia comparable to morphine, yet do not appear to involve the endorphin-enkephalin system, and thus should not be reversed by narcotic antagonists, such as naloxone. It is believed that these compounds will effectively prevent the development of cutaneous hyperalgesia. At high doses, it is believed that these compounds will also exert analgesic activity in classical models of deep pain, elevating the pain threshold above the normal value.

In their anti-irritant activity, these compounds are active against several irritants, including croton oil, and particularly depilatories (thioglycolates). They appear to act, not as protectants or barriers, but, rather, directly to block or eliminate responses to the irritant chemical. In addition, the carbamate derivatives of this invention offer the benefit of reduced discomfort on application. By contrast, compounds such as capsaicin, which possess potent anti-irritant activity, can cause irritation and reddening of the skin.

BACKGROUND ART

J. A. Kiernan, *Quart. J. of Exp. Physiol.*, (1977) 62, 151–161, states that capsaicin, N-(3-methoxy-4-hydroxybenzyl)-8-methyl-6-nonenamide, is known to confer resistance to certain chemical irritants.

Jancso, et al., *Br. J. Pharmac. Chemother.* (1967), 31, 138–151, states that by repeated administration of capsaicin, ocular and/or cutaneous pain receptors can be desensitized to chemical, but not other, stimuli.

Arvier, et al., *Br. J. Pharm.* (1977), 59, 61–68, indicate that capsaicin reduces or blocks the edema formation associated with certain types of inflammation.

DISCLOSURE OF THE INVENTION

The present invention provides compounds of the following formula:

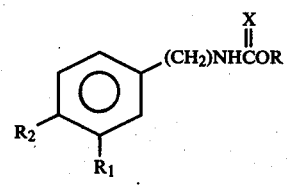

wherein X is O or S, wherein R is $C_3$–$C_{12}$ (preferably $C_6$–$C_{12}$) alkyl or aralkyl, branched or unbranched, aryl or haloaryl, $C_3$–$C_{22}$ (preferably $C_6$–$C_{22}$) alkenyl, branched or unbranched, or benzyl, wherein $R_1$ is H, OH or $OCH_3$ and $R_2$ is H or OH, at least one of $R_1$ and $R_2$ being OH or $OCH_3$; and pharmaceutically acceptable salts thereof. These compounds or salts thereof are hereafter generally referred to as carbamates. The most preferred carbamates are those where X is O, where $R_1$ is $OCH_3$, and where $R_2$ is OH (the N-(3-methoxy-4-hydroxy-benzyl)carbamates), and especially those where R is benzyl or n-octyl. These compounds can be made by synthesis from readily available starting materials, using standard synthetic techniques, as described hereinafter. In the practice of this invention, these carbamates can be administered either topically or systemically.

A. Definitions

By "safe and effective amount" is meant an amount of the carbamate sufficient to provide analgesic or anti-irritant activity so as to alleviate or prevent the pain or irritation being treated at a reasonable benefit/risk ratio attendant with any medical treatment. The amount of the carbamate used will vary with the particular condition being treated, the severity of the condition, the duration of the treatment, the specific formulation employed and the concentration of the carbamate therein, and like factors.

By "systemic administration" is meant introducing the carbamate or composition containing same into the tissues of the body, other than by topical application. Systemic administration thus includes, without limitation, oral, intrathecal, epidural, intramuscular, intravenous, intraperitoneal, and subcutaneous administration.

By "pharmaceutically acceptable" salts is meant those salts which are safe for topical or systemic administration. These include the sodium, potassium, calcium, magnesium, and ammonium salts.

By "topical application" herein is meant directly laying on or spreading the carbamate, or composition containing same, on epidermal or epithelial tissue (including outer skin and oral, gingival, nasal, etc. tissue).

By the term "comprise" as used herein is meant that various other inert ingredients, compatible drugs and medicaments, and steps can be employed in the compositions and processes of this invention as long as the critical carbamates are present in the compositions and are used in the manner disclosed. The term "comprising" thus encompasses and includes the more restrictive terms "consisting essentially of" and "consisting of" which characterize the use of the essential carbamates in the compositions and methods disclosed herein.

By "compatible" herein is meant that the components of the composition are capable of being co-mingled without interacting in a manner which would substantially decrease the efficacy of the total compositions under ordinary use situations.

All percentages herein are by weight of the composition unless otherwise specified.

B. Synthesis of the Carbamates of the Present Invention

The carbamates of this invention can readily be prepared by synthesis along the lines of the following schematic and illustrative examples for the N-(3-methoxy-4-hydroxybenzyl)carbamates.

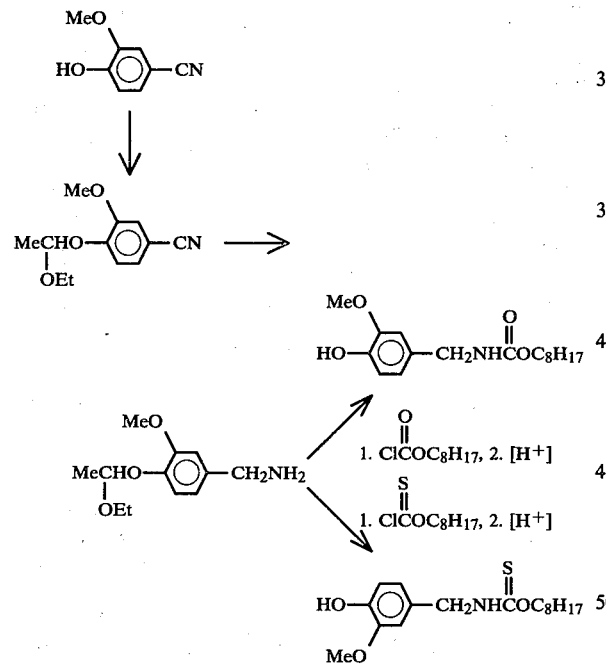

EXAMPLE I

N-(3-methoxy-4-hydroxybenzyl)octylthiocarbamate

A. 3-methoxy-4-(2-ethoxy-1-oxapropyl)benzonitrile

Two ml trifluoroacetic acid was added slowly to a chilled solution of 20 g of 3-methoxy-4-hydroxybenzonitrile, 50.7 ml of ethyl vinyl ether and 50 ml tetrahydrofuran (THF). The mixture was stirred at room temperature overnight. 7.5 ml of triethylamine was added to the mixture and stirring was continued for several minutes followed by solvent evaporation. The residue was partitioned between 400 ml of ether and 100 ml 1 N NaOH. The remaining ether layer was washed with 100 ml $H_2O$ and with 100 ml brine, dried ($MgSO_4$) and evaporated to yield 31.2 gm of crude 3-methoxy-4-(2-ethoxy-1-oxapropyl)benzonitrile.

B. 2-methoxy-4-aminomethyl-(2-ethoxy-1-oxapropyl)benzene

A solution of 5.0 g of 3-methoxy-4-(2-ethoxy-1-oxapropyl)benzonitrile in 25 ml anhydrous THF was added dropwise to 119.5 ml 1 M lithium aluminum hydride in THF. The mixture was refluxed for four hours, cooled to 0° C., and the excess reagent was quenched with 5 N NaOH. The precipitated aluminum salts were removed by filtration and the THF evaporated. The residue was partitioned between 200 ml ether and 75 ml $H_2O$. The remaining ether layer was washed with 75 ml of brine, dried ($K_2CO_3$), filtered, and evaporated to yield 3.63 g of 2-methoxy-4-aminomethyl-(2-ethoxy-1-oxapropyl)-benzene.

C. N-(3-methoxy-4-hydroxybenzyl)octylthiocarbamate

To an ice-cold solution of 4.0 g of 2-methoxy-4-aminomethyl-(2-ethoxy-1-oxapropyl)benzene, 2.09 g of triethylamine and 75 ml $CHCl_3$ was added dropwise a solution of 3.91 g of octyl chlorothioformate and 25 ml $CHCl_3$. The mixture was allowed to warm to room temperature and was stirred for 16 hrs. The reaction mixture was transferred to a separatory funnel and sequentially extracted with 50 ml $H_2O$, 50 ml 1 N HCl, 50 ml $H_2O$, 50 ml saturated $NaHCO_3$, and 50 ml $H_2O$. The resulting $CHCl_3$ was dried ($K_2CO_3$), filtered, and evaporated to yield 7.34 g of crude product. This material was chromatographed on a medium-pressure silica-gel high-performance liquid chromatography column with 25% ethyl acetate/hexane solution which yielded 4.85 g of N-(3-methoxy-4-hydroxybenzyl)octylthiocarbamate, m.p. 63°–64°.

Anal. calc'd for $C_{17}H_{27}NO_3S$: C, 62.75; H, 8.36; N, 4.30; S, 9.85. Found: C 62.75; H, 8.33, N, 4.31; S, 9.92.

EXAMPLE II

N-(3-methoxy-4-hydroxybenzyl)octylcarbamate

A solution of 4.25 g of octylchloroformate and 25 ml of $CHCl_3$ was added dropwise to an ice-cold solution of 4.75 g 2-methoxy-4-aminomethyl-(2-ethoxy-1-oxapropyl)benzene prepared according to Example I, 2.24 g of triethylamine and 75 ml of $CHCl_3$. The mixture was stirred for 16 hrs at room temperature, transferred to a separatory funnel and sequentially extracted with 50 ml 1 N HCl, 50 ml $H_2O$, 50 ml saturated $NaHCO_3$, and 50 ml $H_2O$. The $CHCl_3$ phase was dried ($K_2CO_3$), filtered and evaporated to yield 9.06 g of product. The crude product was dissolved in 70 ml of THF and 25 ml 1 N HCl and stirred for 10 min. The THF was evaporated and the residue dissolved in 125 ml diethyl ether and transferred to a separatory funnel. The small aqueous phase was separated, washed with 25 ml additional ether and then discarded. The ether phases were combined, washed sequentially with 50 ml $H_2O$ and 50 ml brine. The ether solution was dried ($MgSO_4$), filtered, and evaporated to yield 5.84 g of crude product which was recrystallized from 1:1 benzene/hexane to yield 5.3 g of white crystalline solid, m.p. 66°–67°.

Anal. calc'd for $C_{17}H_{27}NO_4$: C, 65.99; H, 8.80; N, 4.53. Found C, 66.07; H, 8.78; N.4.53

By use of the appropriate chloroformate or chlorothioformate in one of the foregoing syntheses, any and all of the compounds of this invention can be prepared.

C. Topical Compositions

The carbamates as previously described are useful when topically applied to skin. Compositions containing these compounds are also useful for topical application to skin. The compositions comprise a safe and effective amount, usually at least about 0.5%, preferably from about 1% to about 2% of the carbamate. The balance of the composition further comprises a pharmaceutically acceptable carrier. Suitable carriers for the carbamate derivatives preferably remain in place on the skin as a continuous film and resist being washed off easily by perspiration or by immersion in water. Generally, the carrier is organic in nature and capable of having dispersed or dissolved therein the carbamate. Lotions, creams, solutions, gels and solids are common physical forms of the compositions herein. A more detailed description of such forms follows.

1. Lotions

The lotions can comprise an effective amount of the carbamate; from 1% to 25%, preferably from 3% to 15%, of an emollient; the balance being water, a $C_2$ or $C_3$ alcohol, or a mixture of water and the alcohol. Several emollients are known. Examples of such emollients are as follows:

1. Hydrocarbon oils and waxes. Examples are mineral oil, petrolatum, paraffin, ceresin, ozokerite, microcrystalline wax, polyethylene, and perhydrosqualene.
2. Silicone oils, such as dimethylpolysiloxanes, methylphenylpolysiloxanes, water-soluble and alcohol-soluble silicone-glycol copolymers.
3. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
7. Alkenyl esters of fatty acids having 10 to 20 carbon atoms. Examples thereof include oleyl myristate, oleyl stearate, and oleyl oleate.
8. Fatty acids having 9 to 22 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.
10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.
13. Polyhydric alcohols and polyether derivatives. Propylene glycol, dipropylene glycol, polypropylene glycol (M.W. 2000-4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200-6000), methoxy polyethylene glycols 350, 550, 750, 2000, 5000, poly[ethylene oxide] homopolymers (M.W. 100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$-$C_{18}$ vicinal glycol, and polyoxypropylene derivatives of trimethylolpropane are examples thereof.
14. Polyhydric alcohol esters. Ethylene glycol mono- and di-fatty acid esters, diethylene glycol mono- and di-fatty acid esters, polyethylene glycol (M.W. 200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
15. Wax esters such as beeswax, spermaceti, myristyl myristate, stearyl stearate.
16. Beeswax derivatives, e.g. polyoxyethylene sorbitol beeswax. These are reaction products of beeswax with ethoxylated sorbitol of varying ethylene oxide content, forming a mixture of ether-esters.
17. Vegetable waxes including carnauba and candelilla waxes.
18. Phospholipids such as lecithin and derivatives.
19. Sterols. Cholesterol, cholesterol fatty acid esters are examples thereof.
20. Amides such as fatty acid amides, ethoxylated fatty acid amides, solid fatty acid alkanolamides.

The lotions further comprise from 1% to 10%, preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the carbamate is dissolved in the mixture. Optional components such as common additives can be included. One common additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite.

2. Creams

Compositions of this invention also can be formulated in a cream form. The creams comprise an effective amount of the carbamate; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The compositions of this invention can be also formulated in a solution form. The solution form comprises an effective amount of the carbamate; the balance being a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in the solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Compositions herein can be formulated into a gel form by simply admixing a suitable thickening agent to the previously described solution compositions. Examples of suitable thickening agents have been previously described with respect to the lotions.

The gelled compositions comprise an effective amount of the carbamate; from 5% to 75%, preferably from 10% to 50%, of an organic solvent as previously described; from 0.5% to 20%, preferably from 1% to 10% of the thickening agent; the balance being water.

5. Solids

The compositions of this invention can also be formulated into a solid form. Such forms have use as a stick-type composition intended for application to the lips or other parts of the body. Such compositions comprise an effective amount of the carbamate and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to the gelled compositions are suitable herein.

Additives commonly found in topical compositions such as preservatives, e.g., methyl and ethyl-paraben, dyes and perfume can be included in any of the previously described compositions.

D. Pharmaceutical Compositions and Dosage Forms for Systemic Administration

The carbamates of the present invention are also useful when used systemically, for example by parenteral administration. The dosage of the carbamate which is both safe and effective to provide analgesic or anti-irritant activity will vary with the particular condition being treated, the severity of the condition, the duration of treatment, the specific carbamate employed and its usage concentration, and like factors within the specific knowledge and expertise of the patient or the attending physician and commensurate with a reasonable benefit/risk ratio associated with the use of any drug compound. The systemic dosages and dosage ranges given herein are based on delivery of the carbamate to a 70 kg human and can be adjusted to provide equivalent dosages for patients of different body weights.

For mammals, especially humans, individual doses of from 0.1 mg to over 100 mg with total dosages of from 0.5 mg to 500 mg are acceptable. Individual doses of from 0.5 mg to 50 mg with total dosages of from 1 mg to 100 mg are preferred. Individual doses of from 5 mg to 25 mg with total dosages of from 10 mg to 50 mg are especially preferred. While dosages higher than the foregoing are effective, toxicity and side effects will present problems in some individuals.

The carbamates can be administered parenterally in combination with a pharmaceutically acceptable carrier such as corn oil, Cremophor EL or sterile, or pyrogen-free water and a water-miscible solvent (e.g., ethyl alcohol) at a practical amount of the carbamate per dose. Parenteral administration can be by subcutaneous, intradermal, intramuscular, intraarticular, or intravenous injection. The dosage by these modes of administration is usually in the range of from about 10 mg. to about 500 mg. per day.

As used herein the term "pharmaceutically acceptable carrier" denotes a solid or liquid filler, diluent, or encapsulating substance. Such examples of substances which can serve as pharmaceutical carriers for the carbamates include: sugars such as lactose, glucose and sucrose; starches such as corn starch and potato starch; cellulose and its derivatives, such as sodium carboxymethylcellulose, ethyl cellulose, cellulose acetate, powdered tragacanth; malt; gelatin; talc, stearic acid magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; sugar; alginic acid; pyrogen-free water; isotonic saline; phosphate buffer solutions; cocoa butter (suppository base), emulsifiers, such as the Tweens® as well as other non-toxic compatible substances typically used on pharmaceutical formulations. Wetting agents and lubricants such as sodium lauryl sulfate, as well as coloring agents, and preservatives, can also be present.

The pharmaceutical carrier employed in conjunction with the carbamate is used at a concentration sufficient to provide a practical size to dosage relationship. Preferably, the pharmaceutical carrier comprises at least about 98% by weight of the total composition.

E. Methods for Providing Analgesia and Anti-irritancy

The present invention encompasses methods for providing analgesia or anti-irritancy in humans or lower animals in need thereof by administering a safe and effective amount, usually from about 10 mg to about 500 mg per patient per day, of the carbamate, usually as a composition with a pharmaceutically acceptable carrier. The carbamates and compositions containing same can be administered by topical application or systemic administration. The carbamates and compositions containing same can be used to treat pain and to provide an analgesic effect in various disorders at the deeper structures, muscles, tendons, bursa and joints associated with disease and trauma, and in various other conditions in which compounds such as aspirin and morphine have heretofore been used to alleviate pain and discomfort.

A "stairstep" dose pattern of sequentially increasing doses is useful for intraperitoneal administration in overcoming temporary side effects and in administering larger doses of the carbamates of this invention. Thus, the initial dose should be selected to provide minimal side effects, and subsequent doses should be increased until the desired level of activity is obtained while still minimizing side effects. In general, an initial dose of 2-10 mg/kg can be conveniently used, followed by doubling of each subsequent dose until the desired level is reached. The doses are preferably separated by a period of at least two hours.

F. Depilatory Compositions Having Reduced Dermal Irritation and Methods for Reducing or Preventing Irritation Caused by Depilatory Agents The present invention also encompasses depilatory compositions having reduced dermal irritation, which comprise: (a) a depilatory amount (e.g. at least about 2%) of a thioglycolate depilatory agent; and (b) the carbamate in an amount effective to reduce the dermal irritation caused by the thioglycolate depilatory agent. The depilatory compositions can be formulated using the pharmaceutically acceptable carriers previously described for topical compositions.

The present invention further encompasses a method for preventing or reducing the dermal irritation caused by a thioglycolate depilatory agent, which comprises the step of applying to at least a portion of a depilated area the carbamate (or composition containing same) in an amount effective to prevent or reduce the irritation caused by treatment of the depilated area with the thioglycolate depilatory agent.

By "thioglycolate depilatory agent" is meant thioglycolic acid, its alkali metal, alkaline earth metal, and ammonium salt(s), or mixtures of the acid and its salt(s).

By "an amount effective to prevent or reduce irritation" is meant an amount of the carbamate (or composition containing same) effective to reduce or prevent the irritation caused by treatment of the depilated area with the thioglycolate depilatory agent at a reasonable benefit/risk ratio. The amount of the carbamate used will vary with the severity of the irritation, the duration of the treatment, the specific formulation employed, the concentration of the sulfonamide therein, and like factors.

By "depilated area" is meant that area which is, or is about to be, depilated by treatment with a thioglycolate depilatory agent.

By the term "applying" with regard to preventing or reducing depilatory irritation is meant the direct laying on or spreading of the carbamate (including compositions containing same) on skin tissue which is, or is about to be depilated. The carbamate can be applied before and/or after treatment of the depilated area with the thioglycolate depilatory agent to prevent or reduce irritation caused thereby. Application of the carbamate to the depilated area after treatment with the depilatory agent is preferred, especially when lower concentrations of the carbamate are used. The number of applications needed to provide effective irritation prevention or reduction can depend upon the concentration of the carbamate used, and when the carbamate is applied in relation to the treatment with the depilatory agent. Application of the carbamate soon after depilation, e.g. within about 6 to about 12 hours, provides effective irritation prevention or reduction, especially in conjunction with additional applications on subsequent days. Multiple applications (2 or more sequential, time spaced applications) soon after depilation are particularly effective. The length of time during which the carbamate is left on the depilated area can also determine its effectiveness. An application duration of at least about 1 hour, preferably from about 1 to about 2 hours, should provide effective irritation prevention or reduction.

Specific Embodiments of Compositions Containing N-(3-Methoxy-4-Hydroxybenzyl)Carbamates The following examples illustrate compositions within the scope of the present invention, but are not limiting thereof.

| Embodiment I Lotion | |
|---|---|
| Isopropyl myristate | 8% |
| Corn oil | 5% |
| Propylene glycol | 5% |
| Triethanolamine oleate | 5% |
| Xanthan gum | 0.5% |
| N—(3-methoxy-4-hydroxybenzyl)hexylthiocarbamate | 0.5% |
| Water | Balance |

| Embodiment II Cream | |
|---|---|
| Isopropyl myristate | 5% |
| Sorbitol | 5% |
| Propylene glycol | 10% |
| Triethanolamine stearate | 17% |
| N—(3-methoxy-4-hydroxybenzyl)dodecylcarbamate | 1% |

-continued

| | |
|---|---|
| Water | Balance |

Embodiment III
Gel

| | |
|---|---|
| Oleyl alcohol | 1% |
| Propylene glycol | 20% |
| Triethanolamine | 0.5% |
| Ethanol | 57% |
| Carbomer 940 | 0.5% |
| N—(3-methoxy-4-hydroxybenzyl) cis-12-docosenylcarbamate | 0.5% |
| Water | Balance |

Embodiment IV
Solution

| | |
|---|---|
| Propylene glycol | 10% |
| Polyethylene glycol 400 | 2% |
| Tween 80$^R$ | 1% |
| Ethanol | 50% |
| N—(3-methoxy-4-hydroxybenzyl) hexenylcarbamate | 1% |
| Water | Balance |

Embodiment V
Ointment

| | |
|---|---|
| Oleyl alcohol | 30% |
| Cetyl alcohol | 40% |
| Propylene glycol | 28% |
| N—(3-methoxy-4-hydroxybenzyl) decylthiocarbamate | 2% |

Effectiveness of N-(3-Methoxy-4-Hydroxybenzyl)Carbamates in Producing Analgesia and in Reducing or Preventing Depilatory Irritation

A. Analgesia

1. Mouse Hot Plate Tests

The Mouse Hot Plate (MHP) model system is designed to detect and evaluate agents which elevate the threshold for the perception of pain. Classically, this method has been utilized primarily to evaluate narcotic type analgesic agents such as morphine. Unless administered in toxic quantities, nonsteroidal anti-inflammatory agents such as aspirin or acetaminophen exhibit little or no activity in this system.

Male CF-1 mice were used. Animals were divided into groups of 8 to 12 and then tested on the "hot plate" to determine their predrug response time which was 4.9 seconds (average). Each animal was then treated with either a test composition (0.5% to 2% of the particular N-(3-methoxy-4-hydroxybenzyl)carbamate in an isotonic saline solution containing ethyl alcohol and Tween 80) or a control composition (same as test composition but without the urea or thiourea). Treatment was by injection prior to test initiation.

2. Procedure

The mice were placed on a 55° C. heated surface and their responses were observed. The endpoint is either a rapid fanning or licking of a paw. To prevent physical injury, the animals were not allowed to remain in contact with the heated surface for more than 60 seconds. The exposure time required to elicit the endpoint response is a measure of the pain threshold. The difference in time required to elicit the endpoint response before and after treatment provides a measure of analgesia. The increase in time required to elicit the endpoint response in treated animals versus control composition is a second measure.

3. Results

The results from the MHP testing of the N-(3-methoxy-4-hydroxybenzyl)carbamates were as follows:

TABLE I

| Compound | Method** | Dosage*** (mg/kg) | Post-Drug Response (sec) |
|---|---|---|---|
| Aspirin* | O | 360 | 6.0 |
| Acetaminophen* | O | 450 | 5.3 |
| Morphine Sulfate* | IP | 13 | 13.1 |
| Morphine Sulfate* | IP | 25 | 17.4 |
| Control | SC | — | 5.0 |
| Octylthiocarbamate | SC | 222 | 8.6 |
| Octylcarbamate | SC | 211 | 7.7 |
| Octylcarbamate | SC | 4,8,15,25, 50,100 | —**** |
| Benzylcarbamate | SC | 196 | 8.6 |

*Commercial Analgesics
**O — oral; SC — subcutaneous; IP — intraperitoneal
***Multiple doses were 2 hours apart
****All animals dead except for one which was not testable The data in Table I shows that N-(3-methoxy-4-hydroxybenzyl)octylthiocarbamate, octylcarbamate and benzylcarbamate have significant analgesic activity relative to the control composition and the commercial analgesics.

B. Preventing or Reducing Depilatory Irritation

A group of 6 male Sprague-Dawley rats weighing 90-115 grams were used for testing the effectiveness of the N-(3-methoxy-4-hydroxybenzyl)carbamates of the present invention in preventing or reducing depilatory irritation. The animals were clipped and depilated with Nair ®, a commercially available thioglycolate depilatory. The test compositions (2% of the N-(3-methoxy-4-hydroxybenzyl)carbamate in an isotonic saline solution containing 48% ethyl alcohol, 4% Tween 80) or a control composition (same as test composition but without the carbamate) were applied to one half (Treated Area) of the depilated area once, 2 hours after depilation on first day; four times, 2 hours apart on second day; and three times, 2 hours apart on third day for a total of eight applications. The duration of each application was 2 hours. The remaining half of the depilated area was left untreated (Untreated Area). Oral ingestion was prevented by the use of "Elizabethan" collars. On the fourth day, the animals were depilated a second time and evaluated for irritation four hours later.

Irritation scores for each animal were determined by visual inspection using the following subjective evaluation scale:

| Score | Description of Irritation |
|---|---|
| 0 | No irritation |
| 0.5 | No scab formation, faint white scale |
| 1.0 | Scab formation (pale orange/orange) over less than 10% of area |
| 2.0 | Mild to moderate intensity scab formation (pale orange) over 10-33% of area |
| 3.0 | Mild to moderate intensity scab formation (pale orange) over 33-75% of area |
| 3.5 | Moderate intensity scab formation (pale orange, occasional deep orange/red) over 75-90% of area |
| 4.0 | Moderate to severe intensity scab formation (deep orange, occasional pale orange) over 90-100% of area |
| 5.0 | Severe intensity scab formation (deep orange/red) over 100% of area |

The irritation scores were totaled for each of the 8-animal groups, the maximum cumulative score being 30. A cumulative score of less than 6 indicated a minimal level of irritation; a score of 6–18 indicated a higher, but acceptable level of irritation; a score of above 18 indicated an unacceptable level of irritation. The results from this testing of the N-(3-methoxy-4-hydroxybenzyl)carbamates were as follows:

TABLE II

| Composition | Cumulative Score | |
|---|---|---|
| | Treated Area | Untreated Area |
| Control | 28 | 28 |
| Benzylcarbamate | 11 | 23 |

The data in Table II shows that N-(3-methoxy-4-hydroxybenzyl)benzylcarbamate was effective in preventing or reducing depilatory irritation in the Treated Area.

What is claimed is:

1. Compounds of formula:

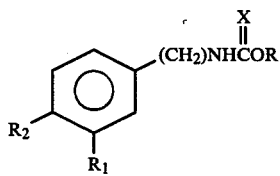

wherein X is O or S, wherein R is $C_3$–$C_{12}$ alkyl or aralkyl, branched or unbranched, aryl or haloaryl, $C_3$–$C_{22}$ alkenyl, branched or unbranched, or benzyl, wherein $R_1$ is H, OH or $OCH_3$ and $R_2$ is H or OH, at least one of $R_1$ and $R_2$ being OH or $OCH_3$; and pharmaceutically acceptable salts thereof.

2. The sodium, potassium, calcium, magnesium, or ammonium salt of the compounds of claim 1.

3. A compound or salt according to claim 1 wherein $R_1$ is $OCH_3$ and wherein $R_2$ is OH.

4. A compound or salt according to claim 3 wherein X is O.

5. A compound according to claim 4 wherein R is $C_6$–$C_{12}$ alkyl or aralkyl, $C_6$–$C_{22}$ alkenyl, or benzyl.

6. A compound or salt according to claim 5 wherein R is benzyl or n-octyl.

7. A compound or salt according to claim 3 wherein X is S and R is n-octyl.

8. A pharmaceutical composition in unit dosage form having analgesic activity which comprises a safe and effective amount of a compound of formula:

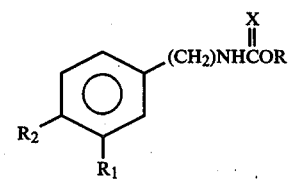

wherein X is O or S, wherein R is $C_3$–$C_{12}$ alkyl or aralkyl, branched or unbranched, aryl or haloaryl, $C_3$–$C_{22}$ alkenyl, branched or unbranched, or benzyl, wherein $R_1$ is H, OH or $OCH_3$ and $R_2$ is H or OH, at least one of $R_1$ and $R_2$ being OH, or a pharmaceutically acceptable salt thereof; and a pharmaceutically acceptable carrier.

9. A composition according to claim 8 wherein the pharmaceutically acceptable salt is a sodium, potassium, calcium, magnesium, or ammonium salt.

10. A composition according to claim 8 wherein $R_1$ is $OCH_3$ and wherein $R_2$ is OH.

11. A composition according to claim 7 wherein X is O.

12. A composition according to claim 11 wherein R is $C_6$–$C_{12}$ alkyl or aralkyl, $C_6$–$C_{22}$ alkenyl or benzyl.

13. A composition according to claim 12 wherein R is benzyl or n-octyl.

14. A composition according to claim 10 wherein X is S and R is n-octyl.

15. A method for providing analgesia in humans and lower animals in need thereof, which comprises the step of administering to the human or lower animal a safe and effective amount of a compound of formula:

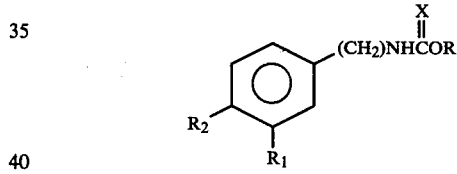

wherein X is O or S, wherein R is $C_3$–$C_{12}$ alkyl or aralkyl, branched or unbranched, aryl or haloaryl, $C_3$–$C_{22}$ alkenyl, branched or unbranched, or benzyl, wherein $R_1$ is H, OH or $OCH_3$ and $R_2$ is H or OH, at least one of $R_1$ and $R_2$ being OH, or a pharmaceutically acceptable salt thereof.

16. A method according to claim 15 in which the compound or salt is administered topically.

17. A method according to claim 15 in which the compound or salt is administered parenterally.

18. A method according to claim 17 in which the compound or salt is administered intramuscularly.

19. A method according to claim 17 in which the compound or salt is administered subcutaneously.

20. A method according to claim 15 in which the compound or salt is administered in sequentially increasing doses.

21. A method according to claim 20 in which the doses are separated by a period of at least 2 hours.

22. A method according to claim 15 wherein $R_1$ is $OCH_3$ and wherein $R_2$ is OH.

23. A method according to claim 22 wherein X is O.

24. A method according to claim 23 wherein R is $C_6$–$C_{12}$ alkyl or aralkyl, $C_6$–$C_{22}$ alkenyl, or benzyl.

25. A method according to claim 22 wherein X is S and R is n-octyl.

* * * * *